(12) United States Patent
Kanca, III

(10) Patent No.: US 7,846,989 B2
(45) Date of Patent: Dec. 7, 2010

(54) DENTAL GEL ETCHANTS

(75) Inventor: John A. Kanca, III, Middlebury, CT (US)

(73) Assignee: John A. Kanca, Middlebury, CT (US)

( * ) Notice: Subject to any disclaimer, the term of this patent is extended or adjusted under 35 U.S.C. 154(b) by 1230 days.

(21) Appl. No.: 11/360,980

(22) Filed: Feb. 23, 2006

(65) Prior Publication Data

US 2007/0009449 A1    Jan. 11, 2007

Related U.S. Application Data

(60) Provisional application No. 60/656,271, filed on Feb. 25, 2005.

(51) Int. Cl.
*A61K 6/00* (2006.01)
*C08K 3/36* (2006.01)

(52) U.S. Cl. ............ 523/118; 524/493; 433/228.1

(58) Field of Classification Search ............ 523/118; 433/228.1; 524/27, 35, 493
See application file for complete search history.

(56) References Cited

U.S. PATENT DOCUMENTS

| | | | |
|---|---|---|---|
| 5,596,025 A * | 1/1997 | Oxman et al. ............ 523/109 |
| 7,041,164 B2 * | 5/2006 | Kanca, III ............ 106/35 |
| 2003/0157034 A1 * | 8/2003 | Jia et al. ............ 424/49 |
| 2004/0229973 A1 * | 11/2004 | Sang et al. ............ 523/118 |
| 2005/0176844 A1 * | 8/2005 | Aasen et al. ............ 523/118 |

OTHER PUBLICATIONS

Kirk-Othmer, Encyclopedia of Chemical Technology, Third Edition, vol. 22, pp. 347-387, 1983.

* cited by examiner

*Primary Examiner*—Tae H Yoon
(74) *Attorney, Agent, or Firm*—Scott D. Rothenberger; Fulbright & Jaworski

(57) ABSTRACT

Etching compositions, curable compositions, packaged products and methods of use for the treatment of bone substrate, i.e., teeth, are described. The etch compositions generally include a gelling agent, an inorganic acid, an organic acid and either a solvent, a surfactant or mixtures thereof. The curable composites include reactive monomers and crosslinking agents that are effective to adhere to the surface of the treated substrate. The methods of the invention provide the ability to modify a bone or bone-like surface so that the curable composition, such as an adhesive resin, can be used in combination with a restorative material.

23 Claims, No Drawings

DENTAL GEL ETCHANTS

CROSS REFERENCE TO RELATED APPLICATIONS

This application claims benefit of U.S. Provisional Patent Application No. 60/656,271, filed on Feb. 25, 2005, which is incorporated by reference in its entirety.

FIELD OF THE INVENTION

The present invention relates to dental gel etching solutions, reactive monomeric based adhesive compositions, packaged pharmaceuticals that contain the gelled etch solution and adhesive composition and methods for their use. More specifically, the present invention relates to a superior two step process, whereby an gel etch composition is applied to a tooth and subsequently causes the dentin to become receptive to adhesive compositions. After the reaction has occurred, the adhesive composition is applied to the tooth and the tooth is readied for a restorative material.

BACKGROUND OF THE INVENTION

The use of biomaterials as restorative materials, in both the dental and medical fields is growing and the requirements for such materials are often times difficult to achieve. Restorative materials such as amalgam or resin composites, are often used to repair dental tissues and bones.

For example, there has been considerable research devoted to the improvement of the adhesion of resins to hard tissues such as dentin or enamel. The adhesives are typically applied to the hard tissue after a pretreatment or etch of the tissue with an acidic solution. Various resin composites are available and generally suffer one or more disadvantages in providing a satisfactory bond between the tissue and the restorative material. Some of adhesive materials are designed to achieve higher bond strengths between tissue layers or the treated tissue and a restorative material, to improve physical properties, or the esthetics of the restored target substrate. Other desired properties of such adhesive composites are directed to their use and include ease in preparation and formulation for use under relatively humid conditions.

Typically an etch solution is utilized to remove the smear layer and demineralize the surface of the dental tissue. The etch solution can alter wettability or chemical reactivity of the pretreated dentin, prior to applying a bonding adhesive agent which is generally a polymerizable monomer. Polymerization of the bonding agent facilitates the bonding agent to adhere to the dentin. The interaction(s) between the bonding agent and the treated substrate is not entirely understood and is believed to be related to chemical, mechanical, interfacial diffusion or a combination of all three physical processes. Polymerization of most bonding adhesives provide an approximately 5 micron thick hybrid layer that is formed of part resin and part dentin. The depth and effectiveness of the penetration of the bonding agent is an important and often critical aspect to the adhesion between the bonding agent and substrate. This hybrid layer is believed to contain little or no apatite and the adhesion to dentin is believed to occur through collagen with the bonding agent.

Even though there has been continued research in the area of etching solutions and bonding agents, the techniques and/or products currently available for pretreating the dental or bone tissue or adhering a restorative material to the bone or dental tissue have limitations. For example, the bonding agents should effectively seal the dentin tubules to prevent post operative sensitivity and protect the pulp. Additionally, the bonds should last the lifetime of the restorative correction and be durable under a variety of conditions.

Therefore, a need exists for new compositions, solutions and methods which overcome one or more of the disadvantages of currently available products.

BRIEF SUMMARY OF THE INVENTION

The present invention provides a unique unexpectedly simple and easy to use bone, i.e., tooth, gel etch composition, a curable adhesive bonding composition, packaged products containing either or both of the compositions, and methods to use the compositions of the invention. The systems of the present invention can be self-cured or can be treated with light energy to facilitate curing.

The present invention provides distinct advantages over presently known etching/bonding systems. Commercially available systems at present include phosphoric acid in the gel, that can cause bleeding in the soft tissue surrounding the treated area.

In one embodiment, the present invention provides a gel etching composition capable of etching bone. In one aspect, the bone is teeth and more specifically, the substrate is dentin, enamel, gum, amalgam, metal, porcelain or plastic. The gel etching composition includes a gelling agent, an inorganic acid, an organic acid, a surfactant, with the remainder being water. The gelling agent is present in an amount of from about 5 parts to about 40 parts by weight. The inorganic acid is present in an amount of from about 1 to about 10 parts by weight. The organic acid is present in amount from about 0.01 to about 20 parts by weight. The surfactant is present in an amount from about 0.01 to about 10 parts by weight and the water is present in an amount to equal a total of 100 parts by weight of all components.

In another embodiment, the present invention provides gel etching compositions that include a gelling agent, an inorganic acid, an organic acid, a solvent and water. The gelling agent is present in an amount of from about parts to about 40 parts by weight. The inorganic acid is present in an amount of from about 1 to about 10 parts by weight. The organic acid is present in amount from about 0.01 to about 20 parts by weight. The solvent is present in an amount from about 1 to about 50 parts by weight, with the water being present in an amount to equal a total of 100 parts by weight of all components.

In another embodiment, the present invention provides gel etching compositions that include a gelling agent, an inorganic acid, an organic acid, an ethylenically unsaturated monomer and water. The gelling agent, inorganic acid and the organic acid are present in the parts described above. The ethylenically unsaturated monomer is present in an amount from about 0.1 to about 10 parts by weight, from about 1.0 to about 5 parts by weight, or from about 2 to about 4 parts by weight, e.g., from about 2 to about 7 parts by weight, e.g., 2.5 parts by weight. The water in the gel etch composition is present in an amount to equal a total of 100 parts by weight of all components. Optionally, a solvent can be added to replace all or part of the aqueous component.

In still another embodiment, the present invention provides gel etching compositions that include a gelling agent, an inorganic acid, an organic acid, an ethylenically unsaturated monomer, a surfactant and water. The gelling agent, inorganic acid, organic acid, ethylenically unsaturated monomer and surfactant are present in the parts described above. The water in the gel etch composition is present in an amount to equal a total of 100 parts by weight of all components. Optionally, a solvent can be added to replace all or part of the aqueous component.

In a particular embodiment, the present invention provides a gel etching composition that includes a gelling agent present in an amount from about 5% to about 40%, i.e., about 10%, a surfactant present in an amount from about 0.01% to about 5%, i.e., about 0.1% of Zonyl® FSN, an inorganic acid present in an amount from about 2% to about 20%, i.e., 5% aqueous stock nitric acid, an organic acid present in an amount from about 2% to about 20%, i.e., about 2.5%, succinic acid, an ethylenically unsaturated monomer present in an amount from about 2% to about 20%, i.e., about 2.5% methacrylic acid with the remainder of the gel composition comprising water equal to 100 parts by weight.

In a specific embodiment, the gel etch composition includes about 5% nitric acid (stock solution), 2.5% methacrylic acid, 2.5% succinic acid, 9% fumed silica (Aerosil® 200), 0.1% Zonyl® FSN and 80.9% water to equal 100 parts by weight.

Suitable components in the gel etching composition include, for example, nitric acid and succinic or citric acid, or combinations thereof, organic solvents such as acetone or lower weight alcohols, and/or various surfactants.

The present invention also pertains to curable composites that include (a) at least one ethylenically unsaturated functional monomer, (b) at least one polyethylenically unsaturated functional crosslinking monomer, (c) a (optionally) fluoride ion agent and (optionally) (d) a solvent. More specifically, the ethylenically unsaturated monomer(s) of (a) is present in an amount of from about 0.5 to about 25 parts by weight. The polyethylenically unsaturated crosslinking monomer(s) of (b) is present in an amount from about 5 to about 40 parts by weight. The optional fluoride agent is present in an amount from about 0.5 to about 5 parts by weight, with the solvent being present in an amount to equal a total of 100 parts by weight of all components.

In certain embodiments, the functional monomer (a) of the curable composition is present in an amount between about 10 parts by weight and about 20 parts by weight. The polyethylenically unsaturated crosslinking monomer (b) is present in an amount between about 18 parts by weight and about 38 parts by weight, and the optional fluoride ion agent is present in an amount between about 0.1 parts by weight and about 10 parts by weight.

Suitable examples of functional monomer(s) (a) include, for example, hydroxyethylmethacrylate, hydroxypropylmethacrylate, and hydroxybutylmethacrylate. Exemplary polyethylenically unsaturated crosslinking monomer(s) (b) include a mixtures of PMGDM and bis-GMA. The optional fluoride ion agent is any source that provides a fluoride ion such as sodium fluoride.

In one particular aspect, the curable composition, the functional monomer (a) is hydroxyethylmethacrylate, the polyethylenically unsaturated crosslinking monomer (b) is a mixture of PMGDM and bis-GMA, and the fluoride ion agent is sodium fluoride. More particularly, the functional monomer (a) is present in an amount of about 15 parts by weight, the first polyethylenically unsaturated crosslinking monomer, PMGDM, is present in an amount of about 20 parts by weight, the second polyethylenically unsaturated crosslinking monomer, bis-GMA, is present in an amount of about 8 parts by weight and the optional sodium fluoride is present in an amount between about 1 and 2 parts by weight.

The curable composition generally includes a photoinitiator system. The photoinitiator system includes a light-sensitive initiator and a polymerization accelerator. A suitable light-sensitive initiator is camphorquinone (CQ) and a suitable polymerization accelerator is ethyl N,N-dimethyl-4-aminobenzoic acid or ethyldimethylaminobenzoic acid (EDMAB).

The present invention further provides packaged formulations of the gel etch compositions, the curable compositions, combinations thereof.

The present invention also provides methods to use the gel etch compositions, alone or in combination with the curable compositions of the invention. It should be understood that the gel etch compositions of the present invention can be used with those commercially available bonding resins. The method of the invention involves applying an effective amount of a gel etching composition to the substrate. The gel etch compositions can be any of the compositions described herein, and for example, can include a gelling agent, an inorganic acid, an organic acid, a solvent and water. The excess gel etching composition can be removed in any manner such that the substrate remains moist. This can be easily accomplished by rinsing the surface with water, or by touching an absorbent material to the treated surface and blotting the excess from the surface. Thereafter, a curable composite is applied to the moist substrate, i.e., a tooth.

The present invention provides a gel etch composition that can be applied to a surface, such as a dental surface, so that the material remains at the point of placement. Typical dental etchants are low viscosity liquids that often spread across the surface and can be hard to control where the liquid travels. This can be problematic where, when applied to a tooth, can advance to the gum line. The typical etch solution can irritate, burn, dry out, cause lesions, blisters, inflammation, etc. to the affected area. The present invention avoids such trauma to the tissue since the gel helps maintain the material at the placement site. The advantageously avoids such known difficulties.

Additionally, the present invention provides an etchant that is easy to handle. Since the etchant is in a gelled form, it is not likely to "spill" or drip onto an undesired surface, such as the tongue, gums or pallet. In contrast, current etch solutions can drip or spill during a procedure since these solutions are less viscous and more difficult to handle by the operator.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

The present invention provides a unique unexpectedly simple and easy to use bone, i.e., tooth, gel etch composition, a curable adhesive bonding composition, packaged products containing either or both of the compositions, and methods to use the compositions of the invention. The present invention provides distinct advantages over presently known etching/bonding systems as described throughout the specification.

In one embodiment, the present invention provides a gel etching composition capable of etching bone. In one aspect, the bone substrate is a tooth and more specifically, the substrate is dentin, enamel, gum, amalgam, metal, porcelain or plastic. The gel etching composition includes a gelling agent, inorganic acid, an organic acid, a surfactant, with the remainder of the solution being water.

The gelling agent is present in an amount of from about 5 parts to about 40 parts by weight. Suitable ranges of the gelling component include from about 7 to about 30 parts by weight, from about 10 to about 20 parts by weight, and from about 12 to about 18 parts by weight.

The inorganic acid is present in the gel etch composition in an amount of from about 1 to about 10 parts by weight. Suitable ranges of inorganic acid include from about 2 to about 9 parts by weight, about 4 to about 8 parts by weight, and about 5 to about 7 parts by weight, i.e. about 6 to about 8 parts by weight. The organic acid is present in the gel etch composition in amount from about 0.01 to about 20 parts by weight. Additional suitable ranges of the organic acid include from about 1 to about 15 parts by weight, 4 to about 12 parts by weight and from about 6 to about 10 parts by weight. The surfactant in the gel etch composition is present in an amount from about 0.01 to about 10 parts by weight, from about 0.1 to about 5 parts by weight or from about 0.5 to about 2.5 parts by weight. The water in the gel etch composition is present in an amount to equal a total of 100 parts by weight of all components.

In another embodiment, the present invention provides gel etching compositions that include a gelling agent, an inorganic acid, an organic acid, a solvent and water. The gelling agent, inorganic acid and the organic acid are present in the parts by weight as described above. The solvent is present in an amount from about 1 to about 50 parts by weight, from about 5 to about 40 parts by weight or from about 10 to about 30 parts by weight. The water in the etch composition is present in an amount to equal a total of 100 parts by weight of all components.

In another embodiment, the present invention provides gel etching compositions that include a gelling agent, an inorganic acid, an organic acid, an ethylenically unsaturated monomer and water. The gelling agent, inorganic acid and the organic acid are present in the parts described above. The ethylenically unsaturated monomer is present in an amount from about 0.1 to about 10 parts by weight, from about 1.0 to about 5 parts by weight, or from about 2 to about 4 parts by weight, e.g., from about 2 to about 7 parts by weight, e.g., 2.5 parts by weight. The water in the gel etch composition is present in an amount to equal a total of 100 parts by weight of all components. Optionally, a solvent can be added to replace all or part of the aqueous component.

In still another embodiment, the present invention provides gel etching compositions that include a gelling agent, an inorganic acid, an organic acid, an ethylenically unsaturated monomer, a surfactant and water. The gelling agent, inorganic acid, organic acid, ethylenically unsaturated monomer and surfactant are present in the parts described above. The water in the gel etch composition is present in an amount to equal a total of 100 parts by weight of all components. Optionally, a solvent can be added to replace all or part of the aqueous component.

In a particular embodiment, the present invention provides a gel etching composition that includes a gelling agent present in an amount from about 5% to about 40%, i.e., about 10%, of a surfactant present in an amount from about 0.01% to about 5%, i.e., about 0.1% of Zonyl® FSN, an inorganic acid present in an amount from about 2% to about 20%, i.e., 5% aqueous stock nitric acid, an organic acid present in an amount from about 2% to about 20%, i.e., about 2.5%, succinic acid, an ethylenically unsaturated monomer present in an amount from about 2% to about 20%, i.e., about 2.5% methacrylic acid with the remainder of the gel composition comprising water equal to 100 parts by weight.

In a specific embodiment, the gel etch composition includes about 5% nitric acid (stock solution), 2.5% methacrylic acid, 2.5% succinic acid, 9% fumed silica (Aerosil® 200), 0.1% Zonyl® FSN and 80.9% water to equal 100 parts by weight.

It should be understood that throughout the specification, the gel etching composition can be utilized on any bone or bone-like substrate that includes, but is not limited to, apatite and hydroxyapatite. Bone is a complex mineralizing system composed of an inorganic or mineral phase, an organic matrix phase, and water. The inorganic mineral phase is composed mainly of crystalline calcium phosphate salts while the organic matrix phase consists mostly of collagen and other noncollagenous proteins.

The phrases "gel etching solution", "gel etch solution", "gel etching composition" and "gel etch composition" are intended to include the compositions of the invention that are gels that superficially dissolve or modify bone or bone-like substrates. For example, in the case of teeth, the gel etch composition removes the smear layer and facilitates demineralization of the surface of the dental tissue.

The terms "comprises" and "comprising" are open ended and are not restrictive in their scope. These terms also include the more restrictive connotations of consisting of and consisting essentially of.

As described above, the gel etch compositions of the present invention include several components. Gelling agents are also known as "thickening agents", and are recognized in the art. Suitable gelling agents for use in the compositions of the invention include those that are known in the art including polyvinylpyrrolidone, carboxypolymethylenes, Pemulen®, Pluronics®, cellulosic ethers, polysaccharide gums, proteins, starches, alignates and fumed silica, i.e., Aerosil® (Degussa).

Polyvinylpyrrolidone, a polymerized polymer of pyrrolidone, is also referred to as "povidone". Polyvinylpyrrolidone is a tertiary amide based polymer. It contains no organic acid in its structure and therefore cannot acid etch or chelate teeth. Polyvinylpyrrolidone is easily dispersed into water to make highly viscous gels for etching at around 5-40% by weight. Polyvinylpyrrolidone may also be considered a tackifying or thickening agent because the increased viscosity of etch composition that it produces has a sticky or tacky feel enabling it to adhere to teeth for the time required to carry out the etching process.

Carboxypolymethylene is a well-known thickening agent that is a slightly acidic vinyl polymer with active carboxyl groups. Suitable carboxypolymethylene compositions may be obtained from B.F. Goodrich Co. under the trade name (CARBOPOL®) as a modified polyacrylic acid hydrophilic polymer, capable of forming viscous gels at concentrations above as little as 5% by weight. These are also referred to as "carbomers".

PEMULEN® is a product of B.F. Goodrich and is used to identify high molecular weight, cross-linked copolymers of acrylic acid and a hydrophobic comonomer. The exact composition of PEMULEN® is unknown since it is a proprietary formulation of B.F. Goodrich.

The term PLURONIC® describes a range of polymers available from BASF, which are also known as poloxamers. The term "poloxamer" is the name for polyoxyethylene polyoxypropylene block copolymers. An example includes POLOXOMER 407, also known as PLURONIC F127.

Alignates include sodium alginate, e.g., Keltone HV, and generally require a cross-linking agent, e.g., a calcium salt, and a sequestrant in order to properly gel. However, when an alkylene glycol alginate is used, neither a calcium salt nor a sequestrant is required in order to gel. The alkylene group may contain from 2 to about 6 carbon atoms. The alkylene glycol alginate should be non-toxic. Preferred is from about 1 to about 15 percent of proylene glycol alginate, which is commercially available as Kelcoloid HVF. When using Kelcoloid HVF, it is preferred to hydrate it first and then add the acid etching solution. The gelling agent is stable in the low pH environment caused by the acid etching composition.

Fumed silica, such as the product offered by Degussa known as AEROSIL®, is an exceptionally pure form of silicon dioxide made by reacting silicon tetrachloride in an oxyhydrogen flame. Particles range from 0.007 to 0.05 µm and tend to link together by a combination of fusion and hydrogen bonding to form chain-like aggregates with high surface areas.

Suitable inorganic acids include nitric acid, sulfuric acid, hydrochloric acid, phosphoric acid and mixtures thereof. In one aspect, the inorganic acid is nitric acid. Nitric acid is generally available as a 70 percent aqueous solution and is utilized at this concentration throughout this application. Sulfuric acid, hydrochloric acid and phosphoric acid are also available as 95-98 percent, 37 percent and 85 percent aqueous solutions, respectively, and are utilized at these concentrations throughout the application. Where noted as parts by weight, this refers to using the concentrated inorganic acid, at the respective commercial concentration, on a weight basis. In certain embodiment of the invention, phosphoric acid is not included as the inorganic acid.

It should be noted that commercially available etch solutions that contain phosphoric acid do not work well in dental applications if the solution is not first rinsed from the substrate to which it is applied. This is due to the precipitation of calcium phosphate from the etch solution that is generated by the reaction of phosphoric acid with the calcium of the bone substrate. The present invention avoids such precipitation by either utilizing a different inorganic acid or by using an organic solvent, surfactant and/or organic acid which inhibit the deposition of calcium phosphate onto the cleaned bone substrate surface.

Suitable organic acids include lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid and mixtures thereof. Other suitable organic acids include 2-acrylamido-2-methylpropane sulfonic acid, benzenesulfonic acid, benzoic acid, bromoacetic acid, 10-camphorquinonesulfonic acid, 10-camphorsulfonic acid, dibromoacetic acid, 2,4-dinitrophenol, formic acid, fumaric acid, 2-hydroxy-4-methoxybenzophenone-5-sulfonic acid, maleic-acid, 2-naphthalene sulfonic acid, nitric acid, oxalic acid, p-nitrophenol, phenol, phosphorous acid esters (such as 2,2'-bis(a-methacryloxy-b-hydroxypropoxyphenyl)propane diphosphonate (Bis-GMA diphosphonate), dibutyl phosphite, di-2-ethyl-hexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), toluene sulfonic acid, tribromoacetic acid, trifluoroacetic acid, trifluoromethanesulfonic acid, and trihydroxybenzoic acid. Mixtures of such acids can be used if desired. In one aspect, the organic acid is succinic acid or citric acid.

The term "surfactant" is recognized in the relevant art to include those compounds which modify the nature of surfaces, e.g. reducing the surface tension of water. Surfactants are generally classified into four types: cationic (e.g. modified onium salts, where part of the molecule is hydrophilic and the other consists of straight or branches long hydrocarbon chains such as hexadecyltrimethyl bromide), anionic, also known as amphiphatic agents (e.g., alkyl or aryl or alkylarylsulfonates, carboxylates, phosphates), nonionic (e.g., polyethylene oxides, alcohols) and ampholytic or amphoteric (e.g. dodecyl-beta-alanine, such that the surfactant contains a zwitterionic group). One or more surfactants can be used in the present invention.

Cationic surfactants useful as surface tension reducing agents in the present invention include long chain hydrocarbons which contain quaternarized heteroatoms, such as nitrogen. Suitable cationic surfactants include quaternary ammonium compounds in which typically one of the groups linked to the nitrogen atom is a C12-C18 alkyl group and the other three groups are short chained alkyl groups.

Anionic surfactants (amphiphatic agents) are characterized by a single lipophilic chain and a polar head group which can include sulfate, sulfonate, phosphate, phosphonate and carboxylate. Exemplary compounds include linear sodium alkyl benzene sulfonate (LAS), linear alkyl sulfates and phosphates, such as sodium lauryl sulfate (SLS) and linear alkyl ethoxy sulfates. Additional examples of anionic surfactants include substituted ammonium (e.g., mono-, di-, and tri-ethanolammonium), alkali metal and alkaline earth metal salts of C6-C20 fatty acids and rosin acids, linear and branched alkyl benzene sulfonates, alkyl ether sulfates, alkane sulfonates, olefin sulfonates, hydroxyalkane sulfonates, fatty acid monoglyceride sulfates, alkyl glyceryl ether sulfates, acyl sarcosinates, acyl N-methyltaurides, and alkylaryl sulfonated surfactants, such as alkylbenzene sulfonates.

Nonionic surfactants do not dissociate but commonly derive their hydrophilic portion from polyhydroxy or polyalkyloxy structures. Suitable examples of polyhydroxy (polyhydric) compounds include ethylene glycol, butylene glycol, 1,3-butylene glycol, propylene glycol, glycerine, 2-methyl-1,3-propane diol, glycerol, mannitol, corn syrup, beta-cyclodextrin, and amylodextrin. Suitable examples of polyalkyloxy compounds include diethylene glycol, dipropylene glycol, polyethylene glycols, polypropylene glycols and glycol derivatives. Some non-ionic surfactants include fluorinated analogs, such as those known by the tradename ZONYL®, manufactured by DuPont.

Other suitable nonionic surfactants include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0-10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Additionally, suitable nonionic surfactants include polyoxyethylene carboxylic acid esters, fatty acid glycerol esters, fatty acid and ethoxylated fatty acid alkanolamides. Block copolymers of propylene oxide and ethylene oxide, and block polymers of propylene oxide and ethylene oxide with propoxylated ethylene diamine are also included as acceptable nonionic surfactants. Semi-polar nonionic surfactants like amine oxides, phosphine oxides, sulfoxides, and their ethoxylated derivatives are included within the scope of the invention.

Suitable amphoteric and zwitterionic surfactants which contain an anionic water-solubilizing group, a cationic group and a hydrophobic organic group include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds Examples of anionic, nonionic, cationic and amphoteric surfactants that are suitable for use in the present invention are described in Kirk-Othmer, Encyclopedia of Chemical Technology, Third Edition, Volume 22, pages 347-387, and McCutcheon's Detergents and Emulsifiers, North American Edition, 1983, both of which are incorporated herein by reference.

Typical concentration ranges of surfactant that are useful in the present gel etch compositions are from about 0.01 parts by weight to about 10 parts by weight, from about 0.1 parts by weight to about 5 parts by weight, and from about 0.5 parts by weight to about 2.5 parts by weight.

The gel etch compositions of the present invention can further include an aldehyde component and in particular a dialdehyde. Suitable aldehydes include formaldehyde, compounds which release formaldehyde, acetaldehyde, propionaldehyde and butyraldehyde and mixtures thereof. Glutaraldehyde is a dialdehyde that is suitable for such use. Suitable ranges of aldehyde or dialdehyde vary from about 0.1 to about 5 parts by weight, from about 0.5 to about 2.5 parts by weight, and from about 1 to about 2 parts by weight.

The terms "solvent" or "organic solvent" are recognized in the art and are intended to mean those components, other than water, that can be added to the gel etch compositions of the invention to help solubilize the components and aid in the evaporation of the etch solution from the substrate surface after application. Suitable solvents include those which are known to be pharmacologically acceptable for treatment of bone tissue. These solvents include dimethyl sulfoxide, ethyl acetate, alcohols and ethers such as methanol, ethanol, propanol, butanol, ethylene glycol, propanediol, butanediol, pentanediol, butenediol, glycerin, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy)ethanol, 2-isopropoxyethanol, 2-butoxyethanol, 1-methoxy-2-propanol, 1-ethoxy-2-propanol, dipropylene glycol, dipropylene glycol monomethyl ether, tripropylene glycol monomethyl ether, glycerine ether and the like, as well as ketones such as acetone, methyl ethyl ketone and the like and mixtures thereof. The solvent is present in an amount from about 1 to about 50 parts by weight, from about 5 to about 40 parts by weight or from about 10 to about 30 parts by weight.

It should be understood that all values, including non-whole values (integers), inclusive, within the ranges of all concentrations (parts by weight) provided throughout this specification are considered individually. That is, it is within the discretion of the operator to choose any percentage within the ranges provided for any of the metal salts as described herein. Therefore, the ranges provided are not limiting in terms of more narrow ranges and individual values that are encompassed by the parameters of the ranges identified.

The gel etch compositions of the present invention can also further include one or more ethylenically unsaturated functional monomers as detailed below. Suitable concentration ranges are from about 5 to about 30 percent, from about 5 to about 20 percent, and from about 7.5 to about 15 percent. In particular, small amounts of such monomers facilitate in the handling and drying aspects of the etch solution. In particular, ethyleneglycol methacrylate phosphate (Aldrich Chemical Company product number 46,333-7) has been found to facilitate both the handling and drying of the etch solution in the above-identified concentration ranges.

The present invention also pertains to curable composites that include (a) at least one ethylenically unsaturated functional monomer, (b) at least one polyethylenically unsaturated functional crosslinking monomer, (c) (optional) a fluoride ion agent and (d) a solvent, with the solvent being present in an amount to equal a total of 100 parts by weight of all components.

The ethylenically unsaturated monomer(s) present in the curable composite resins of the invention (a) is present in an amount of from about 0.5 to about 25 parts by weight, from about 10 to about 20 parts by weight, and from about 12 to about 17 parts by weight.

The phrase "ethylenically unsaturated monomer" includes those reactive agents that include a double bond that can undergo polymerization with other monomers to form a polymeric matrix. The polymerization can be between like monomers or mixtures of monomers. Additionally, the monomers that are ethylenically unsaturated can further react with polyethylenically unsaturated functional crosslinking monomers to form crosslinked networks.

Suitable ethylenically unsaturated monomers, include, but are not limited to ethyleneglycol acrylate phosphate (and methacrylate), 2-hydroxyethylacrylate (HEA), 2-hydroxyethylmethacrylate (HEMA), 2- and 3-hydroxypropylacrylate and methacrylate, 1,3 and 2,3-dihydroxypropylacrylate and methacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, gylcerol monomethacrylate and monoacrylate, various reactive ethylenically unsaturated phosphates, and mixtures thereof. It is considered that where an acrylate monomer is suitable the methacrylate analog will likewise be suitable.

The polyethylenically unsaturated crosslinking monomer (s) of (b) is present in an amount from about 5 to about 40 parts by weight, from about 10 to about 30 parts by weight, and from about 15 to about 25 parts by weight, i.e., about 20 parts by weight.

The phrase "polyethylenically unsaturated functional crosslinking monomer" is recognized in the art and is intended to include those crosslinking agents that have two or more reactive double bonds present within the monomeric backbone. The degree of unsaturation provides the ability to polymerize with other crosslinking agent(s) as well as ethylenically unsaturated monomers to form a network of polymerized material.

Suitable crosslinking monomers include, for example, 2-hydroxypropyl-1,3-diacrylate and dimethacrylate, 3-hydroxypropyl-1,2-diacrylate and dimethylacrylate, pentaerythritol diacrylate and dimethacrylate, triethylene glycol dimethacrylate (TEGDMA) and diacrylate, polyethyleneglycol (400) diacrylate and dimethacrylate, glycerol dimethacrylate and diacrylate and pentaerylthritol trimethacrylate and triacrylate, the reaction product of pyromellitic dianhydride with glycerol dimethacrylate (PMGDM), addition product of 2-hydroxyethyl(meth)acrylate and pyromellitic dianhydride (PMDM), 2,2'-bis[4-(3-methacryloxy-2-hydroxy propoxy)-phenyl]-propane (bis-GMA) and mixtures thereof. In certain aspects of the invention, PMGDM and bis-GMA are preferred.

The term "fluoride agent" is recognized in the art and is intended to include those reagents that provide a fluoride ion. Suitable reagents include fluoride salts, such as sodium fluoride, potassium fluoride, ammonium fluoride, cetyl ammonium fluorides, such as cetyl trialkylammonium fluorides, and mixtures thereof.

The fluoride agent, optionally, is present in an amount from about 0.5 to about 5 parts by weight, from about 1 to about 3 parts by weight, and from about 1 to about 2 parts by weight.

In certain embodiments, the functional monomer (a) of the curable composition is present in an amount between about 10 parts by weight and about 20 parts by weight. The polyethylenically unsaturated crosslinking monomer (b) is present in an amount between about 18 parts by weight and about 38 parts by weight, and the fluoride ion agent is present in an amount between about 0.1 parts by weight and about 10 parts by weight.

Suitable examples of functional monomer(s) (a) include, for example, hydroxyethylmethacrylate, hydroxypropylmethacrylate, and hydroxybutylmethacrylate. Exemplary polyethylenically unsaturated crosslinking monomer(s) (b) include a mixtures of PMGDM and bis-GMA. The optional fluoride ion agent is any source that provides a fluoride ion such as sodium fluoride.

In one particular aspect, the curable composition, the functional monomer (a) is hydroxyethylmethacrylate, the polyethylenically unsaturated crosslinking monomer (b) is a mixture of PMGDM and bis-GMA, and the optional fluoride ion agent is sodium fluoride. More particularly, the functional monomer (a) is present in an amount of about 15 parts by weight, the first polyethylenically unsaturated crosslinking monomer, PMGDM, is present in an amount of about 20 parts by weight, the second polyethylenically unsaturated crosslinking monomer, bis-GMA, is present in an amount of about 8 parts by weight and the sodium fluoride is present in an amount between about 1 and 2 parts by weight.

The curable composition generally includes a photoinitiator system. The photoinitiator system includes a light-sensitive initiator and a polymerization accelerator. A suitable light-sensitive initiator is camphorquinone and a suitable polymerization accelerator is ethyl N,N-dimethyl-4-aminobenzoic acid or N,N-dimethylaminoethyl methacrylate.

Since most of the polymerization reactions which ethylenically unsaturated compounds undergo, particularly acrylate and methacrylate compounds, proceed by a free radical mechanism, a free radical initiator is generally included in the monomer system. Any free radical initiator which is substantially non-toxic in the amounts employed in the composition; which does not react adversely with either the polymeric matrix, once formed, and cures within a few minutes is acceptable. The free radical initiator may be of the chemical type (redox system) in which a peroxide initiator and a polymerization accelerator react at ambient temperatures to initiate the polymerization of the monomer system. Alternatively, a photoinitiator system is used in which light, such as ultraviolet light, but preferably the visible portion of the spectrum, is employed as the energy source to stimulate the free radical initiator.

Examples of such chemical initiators include hydroperoxides, peresters or peroxides such as benzoyl peroxide, or amines, tertiary aromatic amines, such as N,N-dimethyl toluidine can be used. Suitable photoinitiators include benzil 2,3-butanedione, phenyl-1,2-propandione, and camphorquinone (CQ).

Suitable light sources that are effective to cause photoinitiation to occur include halgoen, laser, plasma and LED sources. The amount of energy required, is that amount which is sufficient to initiate a photochemical reaction such that polymerization of the ethylenically unsaturated components is started or enhanced. One skilled in the art can determine the amount of light required to cause such reaction to occur and many light systems are commercially available.

The present invention further provides packaged formulations of the gel etch compositions, the curable compositions, combinations thereof.

For example, the present invention provides a packaged formulation having a gel etching composition including a gelling agent, an inorganic acid, an organic acid, a surfactant and water. The concentrations of the gelling agent, inorganic acid, the organic acid, the surfactant and the water are as provided throughout the present specification. Instructions are provided for the application of the gel etching composition to a bone substrate, i.e., a tooth, such that the substrate is conditioned for further treatment with a curable composition. The instructions provide the length of time to apply the gel etch composition, how to remove the excess, and how to bond a restorative material, e.g., a fixture, to the treated substrate.

The present invention further provides packaged formulations that include a gel etching composition having a gelling agent, an inorganic acid, an organic acid, a solvent and water. The concentrations of the gelling agent, inorganic acid, the organic acid, the solvent and the water are as provided throughout the present specification. Instructions are provided for the application of the gel etching composition to a bone substrate, i.e., a tooth, such that the substrate is conditioned for further treatment with a curable composition. The instructions provide the length of time to apply the gel composition, how to remove the excess, and how to bond a restorative material to the treated substrate.

The present invention also provides packaged formulations that include a gel etching composition that has a gelling agent, an inorganic acid, an organic acid, an ethylenically unsaturated monomer and water. The concentrations of the gelling agent, inorganic acid, organic acid and ethylenically unsaturated monomer are as provided throughout the present specification. Instructions are provided for the application of the gel etching composition to a bone substrate as described throughout the specification.

In another aspect, packaged formulations are provided that include a first container having a gel etching composition and a second container having a curable composition. The gel etching composition includes a gelling agent, an inorganic acid, an organic acid, a surfactant and water. The concentrations of the gelling agent, inorganic acid, the organic acid, the surfactant and the water are as provided throughout the present specification. Instructions are provided for the application of the gel etching composition to a bone substrate, i.e., a tooth, as described previously and throughout the specification.

The second container having the curable composite includes (a) at least one ethylenically unsaturated functional monomer; (b) at least one polyethylenically unsaturated functional crosslinking monomer; (c) (optional) a fluoride ion agent; and (d) a solvent. The concentrations of (a), (b), (c) and (d) are as provided throughout the present specification.

Instructions are also provided for the application of the curable composite to the bone substrate, i.e., a tooth, such that the substrate is conditioned for further treatment with a restorative material.

In still another aspect, packaged formulations are provided that include a first container having a gel etching composition and a second container having a curable composition. The gel etching composition includes a gelling agent, an inorganic acid, an organic acid, a solvent and water. The concentrations of the gelling agent, inorganic acid, the organic acid, the solvent and the water are as provided throughout the present specification. Instructions are provided for the application of the gel etching composition to a bone substrate are as described previously and throughout the specification.

The second container having the curable composite includes (a) at least one ethylenically unsaturated functional monomer; (b) at least one polyethylenically unsaturated functional crosslinking monomer; (c) (optional) a fluoride ion agent; and (d) a solvent. The concentrations of (a), (b), (c) and (d) are as provided throughout the present specification. Instructions are also provided for the application of the curable composite to the bone substrate, i.e., a tooth, such that the substrate is conditioned for further treatment with a restorative material.

Alternatively, the gel etch composition of the first container includes a gelling agent, an inorganic acid, an organic acid, an ethylenically unsaturated monomer and water and/or a solvent. The concentrations of the gelling agent, inorganic acid, organic acid, the ethylenically unsaturated monomer, water, and/or solvent, are as provided throughout the present specification. Instructions are provided for the application of the gel etching composition to a bone substrate, i.e., a tooth, as described previously and throughout the specification.

The containers that can be used for the packaged products are those that are generally commercially available. Any container suitable for retaining the liquids can be used that does not react with the solution(s). The container can be a reusable bottle, as known in the art, a single use bottle or pouch. The container can be collapsible, such as those foil packets known in the art. In certain embodiments, it is advantageous to provide a container that does not permit light to penetrate through the bottle. The solutions can be stored at or below room temperature, so that the container should be to withstand temperatures below room temperature. Bottles or packets prepared from polyethylene or polypropylene are suitable as well as those aluminized foil packets prepared from various terephthalates.

The present invention also provides methods to use the gel etch composition, alone or in combination with the curable compositions of the invention. It should be understood that the gel etch compositions of the present invention can be used with those commercially available bonding resins.

The method of the invention involves applying an effective amount of a gel etching composition to the substrate. The gel etch composition can be any of the gels described herein, and for example, can include a gelling agent, an inorganic acid, an organic acid, a solvent and water. The excess etching gel is removed from the substrate such that the substrate remains moist. This can be easily accomplished by touching an absorbent material to the surface and blotting the excess gel from the surface. Thereafter, a curable composite is applied to the moist substrate, i.e., a tooth. The curable composites of the packaged formulations and methods which follow can further include photoinitiator systems as described throughout the specification.

The present invention also provides methods for adhering a material to a bone substrate, i.e., a dental substrate. The methods generally include applying an effective amount of a gel etching composition that includes a gelling agent, an inorganic acid, an organic acid, a surfactant and water to a substrate, removing excess gel etching composition from the substrate such that the substrate remains moist and applying a curable composite to the moist substrate. The curable composite can be exposed to a light source that emits an effective amount of energy to cure the composite. A restorative material can be adhered to the composite thereafter.

The concentrations of the gelling agent, inorganic acid, the organic acid, the surfactant, the water and the components of the curable composition are as provided throughout the present specification.

In another aspect, the invention provides methods for adhering a material to a bone substrate, i.e., a dental substrate. The methods generally include applying an effective amount of a gel etching composition that includes a gelling agent, an inorganic acid, an organic acid, a solvent and water to a substrate, removing excess gel such that the substrate remains moist and applying a curable composite to the moist substrate. The curable composite can be exposed to a light source that emits an effective amount of energy to cure the composite. A restorative material can be adhered to the composite thereafter.

The concentrations of the gelling agent, inorganic acid, the organic acid, the solvent, the water and the components of the curable composition are as provided throughout the present specification.

In an alternative embodiment, the invention provide methods for adhering a material to a bone substrate as described throughout the specification. The methods generally include application of an effective amount of a gel etch composition that includes a gelling agent, an inorganic acid, an organic acid, an ethylenically unsaturated monomer, water and/or a solvent to a substrate, removing the excess gel such that the substrate remains moist and application of a curable composite to the moist substrate. The curable composite can be exposed to a light source that emits an effective amount of energy to cure the composite. A restorative material can be adhered to the composite thereafter.

The concentrations of the gelling agent, inorganic acid, the organic acid, the solvent, the water and the components of the curable composition are as provided throughout the present specification.

The phrase "effective amount of a gel etching composition" or "effective amount of a dental gel etching composition" is that amount required to modify the surface architecture of the bone substrate. Not to be limited by theory, it is believed that the etching gel removes proteins, lipids, and other foreign materials from the surface of the substrate and penetrates into the substrate. The surface and the penetrated substrate area are cleaned and modified such that they are receptive toward further modification, i.e., a curable composite where reactive functionality such as ethylenic bonds can attach to the modified material. A skilled artisan can readily determine the amount of etching gel to apply to the substrate, however, only enough of the gel is required so as to wet the surface and keep it moist as the surface is modified during application.

The phrases "removing excess gel etching composition" or "removing excess dental gel etching composition" is intended to mean that a sufficient amount of the gel etching solution is removed from the substrate so that the surface remains wetted, i.e., moist. This can be accomplished by a variety of ways, including but not limited to, rising the treated surface with water or contacting the gelled surface with an absorbent material, i.e., a cotton swab or tissue, passing a stream of air over the surface, and other methods known in the art.

In an exemplary method, the substrate material is cleaned with isopropyl alcohol, rinsed with water and dried for a few seconds. The gel composition is applied to the treated surface via a syringe. Alternatively, 1-2 drops of the gel composition are placed in an open well receptacle and a cotton or foam pellet is contacted to the gel. The moistened applicator is contacted to the substrate such that the area to be treated is coated with gel. The applicator is gently agitated with the gel against the surface for at least about 10 to about 30 seconds, i.e., from about 10 to about 30 seconds, from about 10 to about 20 seconds, or from about 10 to about 15 seconds.

Generally, the gel etch composition is allowed to remain on the substrate surface for approximately 10 to about 30 seconds, i.e., from about 10 to about 20 seconds, or from about 10 to about 15 seconds.

After the etching treatment is complete, from about 1 to about 3 coats of an adhesive resin, such as those that are available commercially or those described within the present application, can be applied directly over the moist conditioned preparation with a suitable applicator, such as a brush. The adhesive resin is dried gently, for about 5-8 seconds to facilitate evaporation of the solvent. After the surface is dried, the surface should appear to be "shiny," if not, additional resin adhesive should be applied. The adhesive resin is then light-cured for about 10 seconds. Optionally, a restorative material can be applied to the adhesively treated surface to continue the procedure. However, depending upon what therapeutic treatment is intended, the adhesive resin can serve as a protectant covering and no further restorative treatment may be necessary.

For example, the etching/adhesive system can be used to seal enamel/dentin prior to restoration with light-cured or self-cured composite materials. Indirect Restorations are also encompassed by the present invention and include those preparations when using a light-cured, self-cured or dual-cured composite cement or glass ionomer or resin-modified glass ionomer cement. The methods and compositions of the invention can also be useful for desensitization to treat hypersensitive and/or exposed root surfaces. Additionally, the methods and compositions of the invention can be used to bond in a post and core.

Restorative materials applicable for use with the present invention include those known in the art. Composite materials, synthetic bone materials, bone-like apatite and hydroxyapatite materials are well suited for use with the compositions and methods of the invention. Suitable examples of dental restoratives include composite filling materials, inlays, onlays, crown, bridges, ceramics, veneers and Maryland bridges.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

The experiments that follow were conducted with a gel etchant. The resin, SIMPLICITY 2™, utilized was composed of 25% by weight of PMGDM, 15% by weight HEMA and 8% by weight of bis-GMA with the remainder being solvent and a photo initiator. The method utilized was to apply the gel etch composition to the substrate surface with a syringe or a cotton or foam pellet and gently agitate the gel soaked pellet against the substrate for approximately 10 to about 15 seconds. The gel was rinsed from the surface with an air-water spray. The excess moisture was blotted from the surface with a cotton pellet, leaving the surface moist. The resin composition was then applied to the substrate surface using 2 to 3 coats of the resin. This was dried thoroughly with dried compressed air for about 5 seconds prior to treatment with a restorative material.

The applied resin was light-activated for ten seconds. A teflon mold having a matrix of 2.4 mm diameter and depth of 4 mm was clamped to the tooth. An all-purpose composite (Z100, Minnesota Manufacturing & Mining, Minnesota, USA) was inserted into the matrix and light-activated for 40 seconds. The mold was then removed and the samples stored in water at 37 degrees C. for 24 hours. The samples were then subjected to shear bond strength testing on a Universal testing machine with a crosshead speed of 1 mm/min. The force required to break the composite from the surfaces was recorded in kg and converted to mPa on the basis of the surface area of the sample.

All samples throughout the experiments were prepared prior to testing. The test sample was steam sterilized for 24 hours prior to treatment. The preparation included that a tooth was stabilized and embedded into a cylindrical mounting with a polymerizable monomer, such as methyl methacrylate. The tooth surface was ground until an appropriate surface was exposed, i.e., enamel or dentin. The surface was finely polished, rinsed, dried and then treated. All samples were prepared this way; both with the etch and curable composites of the invention as well as those of competitive products. This was done for consistency between samples.

The following experiments were conducted with a composition of the present invention referred to as APEX GEL ETCHANT™ (also known as APEX GEL ETCH™) or a commercially available etchant. The gel etchant composition referred to as APEX GEL ETCHANT™ was composed of 9% by weight gelling agent, Aerosil 200, 5% by weight nitric acid, 2.5% by weight succinic acid and 2.5% by weight methacrylic acid, with the balance being water. The resin was (SIMPLICITY 2™) 25% by weight PMGDM, 15% by weight HEMA, 8% by weight bis-GMA, 0.5% by weight ethyldimethylaminobenzoic acid (EDMAB) and 0.3% by weight camphoroquinone (CQ), with the balance being acetone. Light-activated systems were preferred as described above. To the resin treated surface was applied a restorative material identified above.

Exemplary results are provided below for the above-described gel etchant and resin system.

Commercial products were utilized for comparison.

A teflon mold having a matrix of 4 mm diameter and depth of 2 mm was clamped to the sample tooth. The all-purpose composite or appropriate material was inserted into the matrix and treated as described above, or by the protocols supplied by the commercial supplier. The mold was then removed and the samples stored in water at 37 degrees C. for 24 hours. The samples were then subjected to shear bond strength testing on a Universal testing machine with a crosshead speed of 5 mm/min. The force required to break the composite from the surfaces was recorded in kg and converted to mPa on the basis of the surface area of the sample.

Light activation was achieved by use of a visible light generating device (Demetron 401 light unit, Demetron-Kerr, Loma Linda, Calif.), that emits wavelengths approximately between about 400 and 500 nanometers (nm) (CQ absorption maximum is about 468 nm). Extra "air thinning" denotes that the resin applied was thinned by drying with compressed air for an extended period of time and with additional force. This causes oxygen inhibition to come into effect and provides for a discrimination between those materials which are more susceptible to oxygen inhibition and those which are not.

In order to compare the commercially available systems to that of the present invention, the method of testing on the final composite was maintained as the same throughout. Unless otherwise noted in the tables, composite samples were prepared with Z100, 3M, St. Paul, Minn. for testing of adhesive/cohesive bond properties.

Apex Gel Etch

The appropriate surface was treated for 15 seconds with APEX GEL ETCHANT™, as described above, rinsed with water for 5 seconds, blotted and treated with SIMPLICITY 2™ followed by activation with visible light for 10 seconds and then the above-described composite material was applied to the treated surface.

| Immediate enamel | 23 mPa |
| Immediate dentin | 29 mPa |

Ultradent Gel Etch

The appropriate surface was treated for 15 seconds with Ultradent gel etch, sold as ULTRA-ETCH™ (a phosphoric acid gel etchant, available from Ultradent, South Jordan, Utah), rinsed with water for 5 seconds, blotted and treated with SIMPLICITY 2™ followed by activation with visibile light for 10 seconds and then the above-described composite material was applied to the treated surface.

| Immediate enamel | 23 mPa |
| Immediate dentin | 29 mPa |

Apex Gel Etch

The appropriate surface was treated for 15 seconds with APEX GEL ETCHANT™, as described above, rinsed with water for 5 seconds, blotted and treated with ONE STEP™ (a resin material available from Bisco, Inc.) followed by activation with visible light for 10 seconds and then the above-described composite material was applied to the treated surface.

| Immediate enamel | 22 mPa |
| Immediate dentin | 28 mPa |

Ultradent Gel Etch

The appropriate surface was treated for 15 seconds with Ultradent gel etch, sold as ULTRA-ETCH™ (a phosphoric acid gel etchant, available from Ultradent, South Jordan, Utah), rinsed with water for 5 seconds, blotted and treated with ONE STEP™ followed by activation with visible light for 10 seconds and then the above-described composite material was applied to the treated surface.

| Immediate enamel | 22 mPa |
| Immediate dentin | 28 mPa |

All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

I claim:

1. A dental gel etching composition comprising
a gelling agent comprising fumed silica;
an inorganic acid;
an organic acid; and
water;
wherein the gelling agent is present in an amount of from about 5 to about 40 parts by weight, the inorganic acid is present in an amount of from about 1 to about 10 parts by weight, the organic acid is present in amount from about 0.01 to about 20 parts by weight, the water being present in an amount to equal a total of 100 parts by weight of all components.

2. The dental gel etching composition of claim 1, wherein the inorganic acid is selected from the group consisting of nitric acid, sulfuric acid, hydrochloric acid and phosphoric acid.

3. The dental gel etching composition of claim 1, wherein the inorganic acid is nitric acid.

4. The dental gel etching composition of claim 3, wherein the nitric acid is present in an amount between about 6 and about 8 parts by weight.

5. The dental gel etching composition of claim 1, wherein the organic acid is selected from the group consisting of lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid.

6. The dental gel etching composition of claim 1, wherein the organic acid is succinic acid.

7. The dental gel etching composition of claim 5, wherein the succinic acid is present in an amount from between about 1.0 and about 3.0 parts by weight.

8. The dental gel etching composition of claim 1, further comprising a solvent.

9. The dental gel etching composition of claim 8, wherein the solvent is present in an amount from about 1 to about 50 parts by weight of the total 100 parts of the composition.

10. The dental gel etching composition of claim 9, wherein the solvent is selected from the group consisting of acetone, dimethyl sulfoxide, and ethanol.

11. The dental gel etching composition of claim 9, wherein the solvent is present in an amount from between about 10 and about 30 parts by weight of the total 100 parts of the composition.

12. The dental gel etching composition of claim 11, wherein the solvent is ethanol.

13. The dental gel etching composition of claim 1, further comprising an ethylenically unsaturated monomer.

14. The dental gel etching composition of claim 13, wherein the ethylenically unsaturated monomer contains a carboxylic acid group.

15. The dental gel etching composition of claim 14, wherein the ethylenically unsaturated monomer is acrylic acid or methacrylic acid.

16. The dental gel etching composition of claim 15, wherein the concentration of the ethylenically unsaturated monomer is present in an amount from between about 5% and about 30% of the total 100 parts of the composition.

17. The dental gel etching composition of claim 1, further comprising a surfactant.

18. The dental gel etching composition of claim 17, wherein the surfactant is a fluorosurfactant.

19. The dental gel etching composition of claim 18, wherein the surfactant is present in an amount from between about 0.01% and about 5% of the total 100 parts of the composition.

20. The dental gel etching composition of claim 13, further comprising a surfactant.

21. The dental gel etching composition of claim 20, wherein the gelling agent is fumed silica, the inorganic acid is nitric acid, the organic acid is succinic acid, the ethylenically unsaturated monomer is methacrylic acid and the surfactant is a fluorosurfactant.

22. The dental gel etching composition of claim 21, wherein the fumed silica is present in an amount from about 5% and about 10%, the nitric acid is present in an amount from about 2% and about 5%, the succinic acid is present in an amount from about 2% and about 5%, the methacrylic acid is present in an amount from about 2% and about 5% and the fluorosurfactant is present in an amount from about 0.01% to about 1%.

23. A packaged formulation comprising:
a dental gel etching composition comprising:
a gelling agent comprising fumed silica;
an inorganic acid;
an organic acid; and
water;
wherein the gelling agent is present in an amount of from about 5 to about 40 parts by weight, the inorganic acid is present in an amount of from about 1 to about 10 parts by weight, the organic acid is present in amount from about 0.01 to about 20 parts by weight, the water being present in an amount to equal a total of 100 parts by weight of all components; and
instructions for application of the dental gel etching composition to a tooth, such that the tooth is conditioned for further treatment with a curable composition.

* * * * *